United States Patent [19]

Drewes et al.

[11] Patent Number: 5,215,569
[45] Date of Patent: Jun. 1, 1993

[54] SUBSTITUTED PYRIDINES

[75] Inventors: Mark W. Drewes, Langenfeld; Peter Müller; Hans-Joachim Santel, both of Leverkusen; Klaus Lürssen; Robert R. Schmidt, both of Bergisch Gladback, all of Fed. Rep. of Germany

[73] Assignee: Bayer Aktiengesellschaft, Leverkusen, Fed. Rep. of Germany

[21] Appl. No.: 738,702

[22] Filed: Jul. 31, 1991

[30] Foreign Application Priority Data

Aug. 10, 1990 [DE] Fed. Rep. of Germany ....... 4025338

[51] Int. Cl.$^5$ .................... C07D 401/12; A01N 43/54
[52] U.S. Cl. ..................... 504/196; 544/122; 544/123; 544/300; 544/310; 544/316; 544/317; 544/243; 544/295; 544/296; 504/243; 504/225; 504/230; 504/242; 504/197; 504/165; 504/168
[58] Field of Search ....................... 71/92, 90; 544/122, 544/123, 300, 310, 316, 317, 243, 295, 296

[56] References Cited

U.S. PATENT DOCUMENTS 5,015,285 5/1991 Rheinheimer et al. ............. 544/311

FOREIGN PATENT DOCUMENTS 0242081 10/1987 European Pat. Off. .
0372329 6/1990 European Pat. Off. .
0374839 6/1990 European Pat. Off. .
0402751 12/1990 European Pat. Off. .

Primary Examiner—John M. Ford
Attorney, Agent, or Firm—Sprung Horn Kramer & Woods

[57] ABSTRACT

Substituted pyridines of the formula

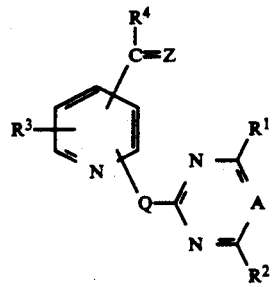

(I)

in which
A represents nitrogen or a C-X group where X represents hydrogen or halogen,
Q represents oxygen or sulphur,
$R^1$ and $R^2$ are identical or different and represent hydrogen, halogen, alkyl, halogenoalkyl, alkoxyalkyl, alkoxy, halogenoalkoxy, alkylthio, alkylamino or dialkylamino,
$R^3$ represents hydrogen, amino, nitro, hydroxyl, halogen, alkyl, halogenoalkyl, alkoxy, halogenoalkoxy, alkylamino, dialkylamino, alkylcarbonylamino, alkoxycarbonylamino or alkylsulphonylamino,
$R^4$ represents hydrogen or alkyl and
Z represents oxygen or one of the groups below:

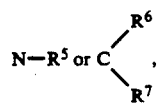

where $R^5$, $R^6$ and $R^7$ are defined herein and their use in herbicide compositions.

7 Claims, No Drawings

SUBSTITUTED PYRIDINES

The invention relates to new substituted pyridines, to processes and to new intermediates for their preparation, and to their use as herbicides.

A series of substituted pyridines which have herbicidal properties has already been disclosed or the subject of general patent claims (cf. EP-A 249,707, EP-A 360,163). However, compounds from the publications mentioned have not gained substantial importance to date.

The new substituted pyridines of the general formula (I) have now been found,

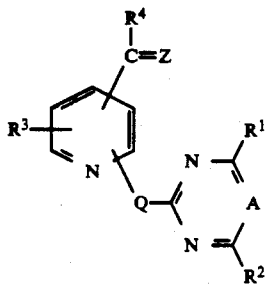

in which
A represents nitrogen or a C-X group where X represents hydrogen or halogen,
Q represents oxygen or sulphur,
$R^1$ and $R^2$ are identical or different and represent hydrogen, halogen, alkyl, halogenoalkyl, alkoxyalkyl, alkoxy, halogenoalkoxy, alkylthio, alkylamino or dialkylamino,
$R^3$ represents hydrogen, amino, nitro, hydroxyl, halogen, alkyl, halogenoalkyl, alkoxy, halogenoalkoxy, alkylamino, dialkylamino, alkylcarbonylamino, alkoxycarbonylamino or alkylsulphonylamino,
$R^4$ represents hydrogen or alkyl and
Z represents oxygen or one of the groups below:

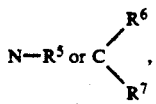

where
$R^5$ represents hydrogen, hydroxyl or amino, or represents in each case optionally substituted alkyl, alkenyl, alkinyl, alkoxy, alkenyloxy, alkoxycarbonylalkoxy, alkylamino, dialkylamino, alkylcarbonylamino, alkoxycarbonylamino, alkylsulphonylamino, aryl, aralkyl, aryloxy, aralkyloxy, arylamino, aralkylamino, N-alkyl-N-arylamino, hetarylamino, hetarylcarbonylamino, arylcarbonylamino or arylsulphonylamino,
$R^6$ represents hydrogen, halogen, cyano, carboxyl, alkoxycarbonyl, alkylcarbonylamino or dialkoxyphosphoryl and
$R^7$ represents formyl, cyano, carboxyl, hydroxymethyl or carbamoyl, or represents in each case optionally substituted alkoxycarbonyl, cycloalkoxycarbonyl, alkylthiocarbonyl, alkylaminocarbonyl, cycloalkylaminocarbonyl, dialkylaminocarbonyl, alkylaminocarbonylalkoxycarbonyl, dialkylaminocarbonylalkoxycarbonyl, arylaminocarbonylalkoxycarbonyl, N-alkyl-N-arylaminocarbonylalkoxycarbonyl, pyrrolidinylcarbonyl, piperidinylcarbonyl, morpholinylcarbonyl, piperazinylcarbonyl, aryloxycarbonyl, aralkyloxycarbonyl, heterocyclylalkoxycarbonyl, arylthiocarbonyl, aralkylthiocarbonyl, arylaminocarbonyl, aralkylaminocarbonyl, N-alkyl-N-arylaminocarbonyl, arylhydrazinocarbonyl, alkylhydrazinocarbonyl, phthalimidoxycarbonyl or $R^7$ together with $R^6$ represents the group $-CO-O-(CH_2)_n-$ where n represents the numbers 1 to 4.

The new substituted pyridines of the general formula (I) are obtained when (a) in the event that, in formula (I), Z represents (a) in the event that, in formula (I), Z represents oxygen and A, Q, $R^1$, $R^2$, $R^3$ and $R^4$ have the abovementioned meaning,
hydroxyalkylpyridines of the general formula (II)

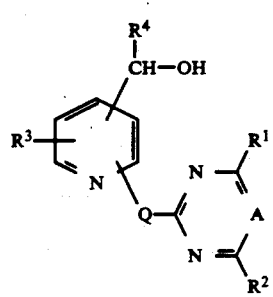

in which A, Q, $R^1$, $R^2$, $R^3$ and $R^4$ have the abovementioned meaning, are reacted with oxidants ("dehydration agents"), if appropriate in the presence of diluents, or when
(b) in the event that, in formula (I), Z represents the group $N-R^5$ or the group

and A, Q, $R^1$, $R^2$, $R^3$, $R^4$, $R^5$, $R^6$ and $R^7$ have the abovementioned meaning,
substituted pyridines of the general formula (Ia)

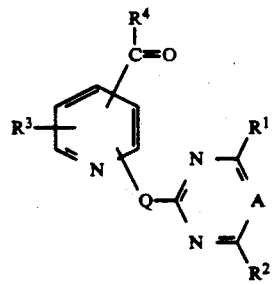

in which A, Q, $R^1$, $R^2$, $R^3$ and $R^4$ have the abovementioned meaning, are reacted with amino or methylene compounds of the general formula (III)

$H_2Z$     (III)

in which Z has the abovementioned meaning,
if appropriate in the presence of a reaction auxiliary and if appropriate in the presence of a diluent, and, if appropriate, the resulting products are subsequently converted by customary methods to give other derivatives in accordance with the definition of the compounds of the formula (I).

The new substituted pyridines of the general formula (I) are distinguished by a powerful herbicidal activity.

Preferred substituents or areas of the radicals given in the formulae mentioned above and below were illustrated in what follows:

In the general formulae, alkyl on its own or in composite radicals such as, for example, alkylamino or alkoxycarbonylalkyl, represents alkyl having preferably 1 to 6, particularly preferably 1 to 4 and especially 1 to 2 carbon atoms. The following may preferably be mentioned by way of example: methyl, ethyl, n- and iso-propyl, and n-, i-, s- and tert.-butyl.

In the general formulae, alkoxy and alkylthio on their own or in composite radicals such as, for example, alkoxycarbonyl or alkylthiocarbon-ylalkyl, represent alkoxy, or alkylthio, having preferably 1 to 6, particularly preferably 1 to 4, and especially preferably 1 to 2 carbon atoms. The following may preferably be mentioned by way of example: methoxy, ethoxy, n- and i-propoxy, n-, i-, s- and tert.-butoxy, methylthio, ethylthio, n- and i-propylthio, n-, i-, s- and tert.-butylthio.

In the general formulae, alkenyl and alkinyl on their own or in composite radicals represent alkenyl, or alkinyl, having preferably 3 to 6, particularly preferably 3 or 4, carbon atoms. The following may preferably be mentioned by way of example: allyl and propargyl.

In the general formulae, halogenoalkyl, halogenoalkoxy and halogenoalkylthio represent in each case straight-chain or branched halogenoalkyl, halogenoalkoxy or halogenoalkylthio having 1 to 4, and preferably 1 or 2, carbon atoms and in each case 1 to 9 and preferably 1 to 5, identical or different halogen atoms as defined under halogen; the following may preferably be mentioned by way of example: fluoromethyl, chloromethyl, bromomethyl, fluoroethyl, chloroethyl, bromoethyl, fluoro-n.-propyl, chloro-n-propyl, dichloromethyl, difluoroethyl, trifluoroethyl, trichloroethyl, trifluorochloroethyl, chlorobutyl, fluorobutyl and, especially, difluoromethyl, trifluoromethyl, trichloromethyl, dichlorofluoro-methyl and chlorodifluoromethyl, and the corresponding halogenoalkoxy radicals or halogenoalkylthio radicals.

The definitions mentioned here are also true, in a corresponding manner, for the preferred combinations of radicals mentioned below.

The invention preferably relates to compounds of the formula (I) in which

A represents nitrogen or a C-X group, where X represents hydrogen or halogen,

Q represents oxygen or sulphur, $R^1$ and $R^2$ are identical or different and represent hydrogen, halogen, $C_1-C_4$-alkyl, $C_1-C_4$-halogenoalkyl, $C_1-C_2$-alkoxy-$C_1-C_2$-alkyl, $C_1-C_4$-alkoxy, $C_1-C_4$-halogenoalkoxy, $C_1-C_4$-alkylthio, $C_1-C_4$-alkylamino or di-($C_1-C_2$-alkyl)-amino, $R^3$ represents hydrogen, amino, nitro, hydroxyl, halogen, $C_1-C_4$-alkyl, $C_1-C_4$-halogenoalkyl, $C_1-C_4$-alkoxy, $C_1-C_4$-halogenoalkoxy, $C_1-C_4$-alkylamino, di-($C_1-C_2$-alkyl)-amino, $C_1-C_4$-alkyl-carbonylamino, $C_1-C_4$-alkoxy-carbonylamino or $C_1-C_4$-alkylsulphonylamino, $R^4$ represents hydrogen or $C_1-C_4$-alkyl and Z represents oxygen or one of the groups below: N-$R^5$ or

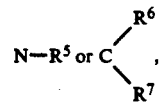

where $R^5$ represents hydrogen, hydroxyl or amino, or represents in each case optionally halogen-substituted $C_1-C_6$-alkyl, $C_3-C_6$-alkenyl, $C_3-C_6$-alkinyl, $C_1-C_6$-alkoxy, $C_3-C_6$-alkenyloxy, $C_1-C_4$-alkoxy-carbonyl-$C_1-C_2$-alkoxy, $C_1-C_6$-alkyl-amino, di-($C_1-C_2$-alkyl)-amino, $C_1-C_6$-alkyl-carbonylamino, $C_1-C_6$-alkoxy-carbonylamino, $C_1-C_6$-alkyl-sulphonylamino, or represents phenyl, phenyl-$C_1-C_4$-alkyl, phenoxy, phenyl-$C_1-C_4$-alkoxy, phenylamino, phenyl-$C_1-C_4$-alkylamino, N-($C_1C_4$-alkyl)-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, amino, cyano, carboxyl, halogen, $C_1-C_4$-alkyl, $C_1-C_2$-halogenoalkyl, $C_1-C_4$-alkoxy, $C_1-C_2$-halogenoalkoxy, $C_1-C_4$-alkylthio, $C_1-C_2$-halogenoalkylthio, $C_1-C_4$-alkoxy-carbonyl and/or di-($C_1-C_2$-alkyl)-amino, $R^6$ represents hydrogen, halogen, cyano, carboxyl, $C_1-C_6$-alkoxy-carbonyl, $C_1-C_6$-alkylcarbonylamino or di-($C_1-C_4$-alkoxy)-phosphoryl and $R^7$ represents formyl, cyano, carboxyl, hydroxymethyl or carbamoyl, or represents $C_1-C_6$-alkoxy-carbonyl, $C_5-C_6$-cycloalkyloxy-carbonyl, $C_1-C_6$-alkylthio-carbonyl, $C_1-C_6$-alkylamino-carbonyl or $C_5-C_6$-cycloalkylamino-carbonyl, each of which is optionally substituted by halogen, carboxyl or $C_1-C_4$-alkoxy-carbonyl, or represents di-($C_1-C_2$-alkyl)-amino-carbonyl, or represents $C_1-C_4$-alkylamino-carbonyl-$C_1-C_4$-alkoxy-carbonyl, or represents di-($C_1-C_2$-alkyl)-amino-carbonyl-$C_1-C_4$-alkoxy-carbonyl, or represents phenylaminocarbonyl-$C_1-C_4$-alkoxy-carbonyl, or represents N-methyl-N-phenylaminocarbonyl-$C_1-C_4$-alkoxy-carbonyl, or represents pyrrolidinylcarbonyl, piperidinyl-carbonyl, morpholinylcarbonyl or piperazinylcarbonyl, each of which is optionally substituted by methyl and/or ethyl, or represents phenoxycarbonyl, phenyl-$C_1-C_4$-alkoxycarbonyl, furylmethoxycarbonyl, thienylmethoxycarbonyl, phenylthiocarbonyl, phenyl-$C_1-C_4$-alkylthiocarbonyl, phenylaminocarbonyl, phenyl-$C_1-C_4$-alkylamino-carbonyl, N-($C_1-C_4$-alkyl)-N-phenylamino-carbonyl or phenylhydrazinocarbonyl or $C_1-C_4$-alkylhydrazinocarbonyl, each of which is optionally substituted by nitro, amino, cyano, carboxyl, halogen, $C_1-C_4$-alkyl, $C_1-C_2$-halogenoalkyl, $C_1-C_4$-alkoxy, $C_1-C_2$-halogenoalkoxy, $C_1-C_4$-alkylthio, $C_1-C_2$-halogeno-alkylthio, $C_1-C_4$-alkoxy-carbonyl and/or di-($C_1-C_2$-alkyl)amino, or represents phthalimidoxycarbonyl, or together with $R^6$ represents the group —CO—O—(CH$_2$)$_n$—, where n represents the numbers 1 to 4, especially 2 or 3.

The aliphatic hydrocarbon radicals (for example alkyl, alkenyl, alkinyl), also in combination with hetero atoms (for example in alkoxy, alkylthio or alkylamino) or in compositions such as, for example, halogenoalkyl or halogenoalkoxy, which are mentioned in the definition of the compounds according to the invention, are in each case straight-chain or branched.

Halogen generally represents fluorine, chlorine, bromine or iodine, preferably fluorine, chlorine or bromine, especially fluorine or chlorine The invention especially relates to compounds of the formula (I) in which A represents nitrogen or a CH group, Q represents oxygen, $R^1$ represents hydrogen, chlorine, methyl, ethyl, trifluoromethyl, methoxymethyl, methoxy, ethoxy, difluoromethoxy, methylthio, methylamino, ethylamino or dimethylamino, $R^2$ represents hydrogen, chlorine, methyl, ethyl, trifluoromethyl, methoxy, ethoxy, difluoromethoxy, methylthio, methylamino, ethylamino or dimethylamino, $R^3$ represents hydrogen, amino, hydroxyl, fluorine, chlorine, bromine, methyl, ethyl, trifluoromethyl, methoxy, difluoromethoxy, trifluoromethoxy, methylamino, dimethylamino, acetylamino, methoxycarbonylamino, or methylsulphonylamino, $R^4$ represents hydrogen or methyl and Z represents oxygen or one of the groups below:

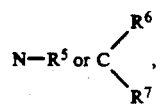

where $R^5$ represents hydrogen, hydroxyl or amino, or represents methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenoxy, benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, cyano, fluorine, chlorine, bromine, methyl, trifluoromethyl, methoxy, trifluoromethoxy, methylthio or trifluoromethylthio, $R^6$ represents hydrogen, fluorine, chlorine, cyano, carboxyl, $C_1$–$C_4$-alkoxy-carbonyl, $C_1$–$C_4$-alkylcarbonylamino, dimethoxyphosphoryl or diethoxyphosphoryl, and $R^7$ represents formyl, cyano, carboxyl, hydroxymethyl or carbamoyl, or represents $C_1$–$C_4$-alkoxy-carbonyl, $C_5$–$C_6$-cycloalkyloxy-carbonyl, $C_1$–$C_4$-alkylthiocarbonyl, $C_1$–$C_4$-alkylamino-carbonyl or $C_5$–$C_6$-cycloalkylamino-carbonyl, each of which is optionally substituted by fluorine, chlorine, carboxyl or $C_1$–$C_4$-alkoxy-carbonyl, or represents dimethylaminocarbonyl, or represents $C_1$–$C_4$-alkylaminocarbonyl-$C_1$–$C_4$-alkoxy-carbonyl, or represents dimethylaminocarbonyl-$C_1$–$C_4$-alkoxy-carbonyl, or represents N-methyl-N-phenylaminocarbonyl-$C_1$–$C_4$-alkoxy-carbonyl, or represents pyrrolidinylcarbonyl, piperidinyl-carbonyl, morpholinylcarbonyl or piperazinyl-carbonyl, each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl, phenylhydrazinocarbonyl, each of which is optionally substituted by nitro, cyano, fluorine, chlorine, bromine, methyl, trifluoromethyl., methoxy, trifluoromethoxy, methylthio or trifluoromethylthio, or represents phthalimidoxycarbonyl, or together with $R^6$ represents the group —CO—O—$CH_2CH_2$—.

Particularly preferred groups of compounds of the formula (I) are those of the formulae (IA) and (IB) below in which A, Q, $R^1$, $R^2$, $R^3$, $R^4$ and Z in each case have the meanings given above as being especially preferred. The group (IA) may be especially emphasised.

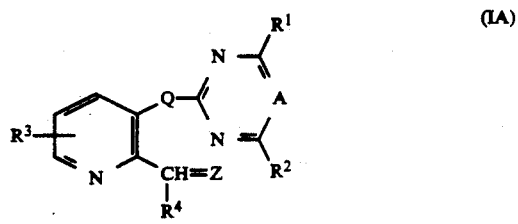

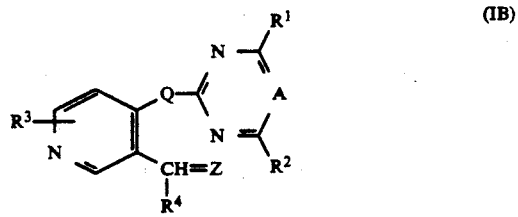

Very particularly preferred compounds of the formula (I), in particular of the formulae (IA) and (IB), are those in which A represents a CH group, Q represents oxygen, $R^1$ represents methoxy, $R^2$ represents methoxy, $R^3$ represents hydrogen or fluorine, $R^4$ represents hydrogen and Z has the meaning given above as being especially preferred.

The following meanings for $R^5$ must be particularly emphasised: Hydrogen, hydroxyl, amino, methyl, ethyl, n-propyl, i-propyl, n-butyl, i-butyl, sec-butyl, tert.-butyl, methylamino, ethylamino, n-propylamino, i-propylamino, n-butylamino, i-butylamino, sec-butylamino, tert.-butylamino, dimethylamino, acetylamino, propionylamino, methoxycarbonylamino or ethoxycarbonylamino, or phenyl, benzyl, phenylamino, benzylamino, or N-methyl-N-phenylamino, each of which is monosubstituted to trisubstituted by identical or different substituents from the series comprising fluorine, chlorine, nitro, cyano, methyl, trifluoromethyl, methoxy and trifluoromethoxy.

The following meanings for $R^6$ must be particularly emphasised: Hydrogen, cyano, carboxyl and $C_1$–$C_4$-alkoxy-carbonyl.

The following meanings for R must be particularly emphasised: Cyano, carboxyl and $C_1$–$C_4$-alkoxy-carbonyl.

If, for example, 3-(4,6-dimethoxy-pyrimidin-2-yl-oxy)-2-hydroxymethyl-pyridine and manganese(IV) oxide are used as starting substances in process (a) according to the invention for the preparation of the compounds of the formula (I), the course of the reaction can be illustrated by the following equation:

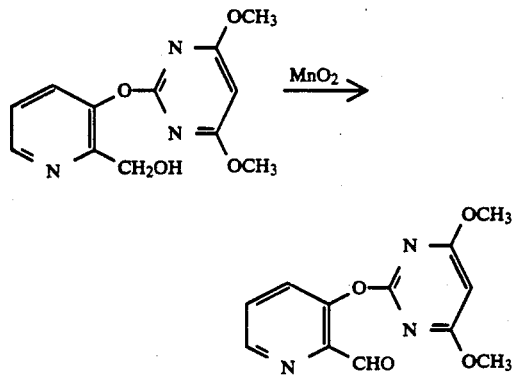

If, for example, 3-(4-methoxy-6-methyl-pyrimidin-2-yl-oxy)-2-formyl-pyridine and hydroxylamine are used as starting substances in process (b) according to the invention for the preparation of the compounds of the formula (I), the course of the reaction can be illustrated by the following equation:

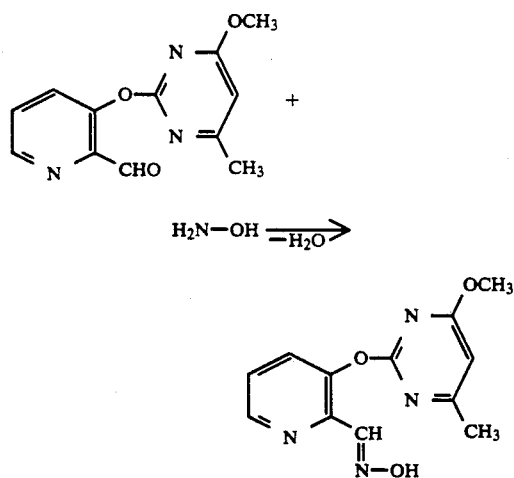

Formula (II) provides a general definition of the hydroxyalkylpyridines to be used as starting substances in process (a) according to the invention for the preparation of compounds of formula (I).

In formula (II), A, Q, $R^1$, $R^2$, $R^3$ and $R^4$ preferably, or especially, have those meanings which have already been indicated above in connection with the description of the compounds of the formula (I) according to the invention as being preferred, or especially preferred, for A, Q, $R^1$, $R^2$, $R^3$ and $R^4$.

Examples of the starting substances of the formula (II) which may be mentioned are: 3-(4,6-dimethyl-pyrimidin-2-yl-oxy)-, 3-(4-methoxy-6-methyl-pyrimidin-2-yl-oxy)-, 3-(4,6-dimethoxy-pyrimidin-2-yl-oxy)-, 3-(4-methoxy-6-trifluoromethyl-pyrimidin-2-yl-oxy)-, 3-(4,6-dimethyl-s-triazin-2-yl-oxy)-, 3-(4-methoxy-6-methyl-s-triazin-2-yl-oxy)- and 3-(4,6-dimethoxy-s-triazin-2-yl-oxy)-2-hydroxymethyl-pyridine.

The hydroxyalkylpyridines of the formula (II) were hitherto not known from the literature and also a subject of the present application. The new compounds of the formula (II) are obtained when pyridinecarboxylic acid derivatives of the general formula (IV)

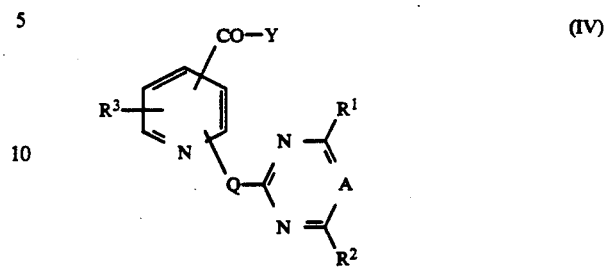

in which

A, Q, $R^1$, $R^2$ and $R^3$ have the abovementioned meaning and

Y represents halogen, hydroxyl or alkoxy, are reacted with metal compounds of the general formula (V)

in which $R^4$ has the abovementioned meaning and

M represents a metallic or metal-containing component which is customary in the case of (optionally complex) metal hydrides or organometal compounds, if appropriate in the presence of a diluent such as, for example, diethyl ether, dimethoxyethane, tetrahydrofuran, methanol, ethanol or isopropanol, at temperatures between $-70°$ C. and $+50°$ C., and the product is worked up by customary methods (cf. preparation examples).

In formula (IV), A, Q, $R^1$, $R^2$ and $R^3$ preferably, or especially, have those meanings which has already been mentioned above in connection with the description of the compounds of the formula (I) according to the invention as being preferred, or especially preferred, for A, Q, $R^1$, $R^2$ and $R^3$, and Y preferably represents chlorine, hydroxyl, methoxy or ethoxy.

Examples of the starting substances of the formula (IV) which may be mentioned are: 3-(4,6-dimethyl-pyrimidin-2-yl-oxy)-, 3-(4-methoxy-6 -methyl-pyrimidin-2-yl-oxy)-, 3-(4,6-dimethoxy-pyrimidin-2-yl-oxy)-, 3-(4-methoxy-6-trifluoromethyl-pyrimidin-2-yl-oxy)-, 3-(4,6-dimethyl-s-triazin-2-yl-oxy)-, 3-(4-methoxy-6-methyl-s-triazin-2-yl-oxy)- and 3-(4,6-dimethoxy-s-triazin-2-yl-oxy)-pyridin-2-carboxylicacid and the corresponding carboxylic acid chlorides, the methyl esters and the ethyl esters.

The pyridine carboxylic acid derivatives of the formula (IV) are known and/or can be prepared by processes known per se (cf. EP-A 249,707).

In formula (V), $R^4$ preferably, or especially, has the meaning which has already been mentioned above in connection with the description of the compounds of the formula (I) according to the invention as being preferred, or especially preferred, for $R^4$, and M preferably represents a metal from the series comprising lithium, sodium, potassium, magnesium, calcium, boron and aluminium, to which, if appropriate (if polyvalent), hydrogen atoms, alkali metal atoms or halogen atoms are bonded additionally.

Examples of the compounds of the formula (V) which may be mentioned are: lithium hydride, sodium hydride, potassium hydride, magnesium hydride and calcium hydride, lithium tetrahydridoborate, sodium tetrahydridoborate and potassium tetrahydridoborate ("borohydride", "boranate"), lithium tetrahydridoaluminate, sodium tetrahydridoaluminate and potassium tetrahydridoaluminate ("alanate"), methyllithium, butyllithium, methylmagnesium chloride, methylmagnesium bromide and methylmagnesium iodide, ethylmagnesium chloride-bromide, propylmagnesium chloridebromide and isopropylmagnesium chloridebromide and ethylmagnesium iodide, propylmagnesium iodide and isopropylmagnesium iodide.

The compounds of the formula (V) are known chemicals for synthesis.

Process (a) according to the invention is carried out using oxidants. Oxidants which are preferably employed for this purpose are substances which are customarily used for dehydrating alcohols to give aldehydes or ketones such as, for example, manganese(IV) oxide ("manganese dioxide"), dimethyl sulphoxide/oxalyl chloride (Swern's reagent), chromium(VI) oxide or sodium dichromate/sulphuric acid.

Process (a) according to the invention for the preparation of the new substituted pyridines of the formula (I) is preferably carried out using diluents. Diluents which are suitable for this purpose are virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methyl-pyrrolidone, and also dimethyl sulphoxide, tetramethylene sulphone and hexamethylphosphoric triamide.

When carrying out process (a) according to the invention, the reaction temperatures can be varied within a substantial range. In general, the process is carried out at temperatures between $-80°$ C. and $+150°$ C., preferably at temperatures between $-60°$ C. and $+100°$ C.

In general, process (a) according to the invention is carried out under atmospheric pressure. However, it is also possible to carry out the process under increased or reduced pressure.

For carrying out process (a) according to the invention, between 1 and 50, preferably between 1 and 25, mole equivalents of the oxidant are generally employed per mole of hydroxyalkylpyridine of the formula (II).

In general, the starting compound of the formula (II) is first introduced into a suitable diluent and the oxidant is slowly added to this mixture. The reaction mixture is stirred at the temperature required until the reaction is complete and worked up in the customary manner (cf. preparation examples).

Formula (Ia) provides a general definition of the substituted pyridines to be used as starting substances in process (b) according to the invention for the preparation of compounds of the formula (I).

In formula (Ia), A, Q, $R^1$, $R^2$, $R^3$ and $R^4$ preferably, or especially, have those meanings which have already been mentioned above in connection with the description of the compounds of the formula (I) according to the invention as being preferred, or especially preferred, for A, Q, $R^1$, $R^2$, $R^3$ and $R^4$.

The substituted pyridines of the formula (Ia) are new compounds according to the invention; they can be prepared by process (a) according to the invention.

Formula (III) provides a general definition of the amino or methylene compounds furthermore to be used as starting substances in process (b) according to the invention for the preparation of compounds of the formula (I).

In formula (III), Z preferably, or especially, has the meaning which has already been mentioned above in connection with the description of the compounds of the formula (I) according to the invention as being preferred, or especially preferred, for Z, with the exception of oxygen. Examples of the starting substances of the formula (III) which may be mentioned are: ammonia, hydroxylamine, hydrazine, methylamine, ethylamine, propylamine, isopropylamine, butylamine, isobutylamine, sec-butylamine, tert-butylamine, allylamine, propargylamine, O-methyl-, O-ethyl-, O-propyl-, O-isopropyl-, O-butyl-, O-isobutyl- and O-sec-butyl-hydroxylamine, O-allyl-hydroxylamine, methyl aminooxyacetate and ethyl aminooxyacetate, methyl α-aminooxypropionate and ethyl α-aminooxy-propionate, methylhydrazine, ethylhydrazine, propylhydrazine, isopropylhydrazine, butylhydrazine, isobutylhydrazine, sec-butylhydrazine, tert-butylhydrazine, N-N-dimethylhydrazine, acethydrazide, propionylhydrazide, methoxycarbonylhydrazine, ethoxycarbonylhydrazine, methylsulphonylhydrazine, ethylsulphonylhydrazine, phenylhydrazine, benzoylhydrazine, benzenesulphonohydrazide, p-toluenesulphonohydrazide, malonic acid, cyanoacetic acid, malononitrile, methyl cyanoacetate and ethyl cyanoacetate, dimethyl malonate and diethyl malonate, and γ-butyrolactone.

The starting substances of the formula (III) are known chemicals for synthesis.

Process (b) according to the invention for the preparation of the new substituted pyridines of the formula (I) is preferably carried out using diluents. Diluents which are suitable for this purpose are, besides water, virtually all inert organic solvents. These preferably include aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoric triamide.

If appropriate, process (b) according to the invention is carried out in the presence of a reaction auxiliary. Suitable reaction auxiliaries are substances which are customarily used for controlling and/or accelerating condensation reactions between carbonyl compounds and amino or methylene compounds. They especially include nitrogen compounds such as, for example, ammonium acetate, β-alanine, pyridine and piperidine.

When carrying out process (b) according to the invention, the reaction temperatures can be varied within a substantial range. In general, the process is carried out at temperatures between 0° C. and 150° C., preferably at temperatures between 10° C. and 120° C.

Process (b) according to the invention is generally carried out under atmospheric pressure. However, it is also possible to carry out the process under increased or reduced pressure.

For carrying out process (b) according to the invention, the starting substances required in each case are generally employed in approximately equimolar amounts. However, it is also possible to use one of the two components employed in each case in a larger excess. In general, the reactions are carried out in a suitable diluent, if appropriate in the presence of a reaction auxiliary, and the reaction mixture is stirred for several hours at the particular temperature required. Working-up in the process according to the invention is carried out in each case by customary methods (compare the preparation examples).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

The compounds of the formula (I) according to the invention are especially suitable for selectively combating monocotyledon and dicotyledon weeds by the pre-emergence and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene, or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl-)-N,N'-dimethylurea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in sugar beet and 4-amino-6-(1,1-dimethylethyl)-3-methylthio-1,2,4-triazin-5(4H)-one for combating weeds in soya beans; furthermore also 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); 2-chloro-4-ethylamino-6-isopropylamino-1,3,5-triazine (ATRAZINE); 3-isopropyl-2,1,3-benzothiadiazin-4-one 2,2-dioxide (BENTAZONE); methyl 5-(2,4-dichlorophenoxy)-2-nitrobenzoate (BIFENOX); 3-5-dibromo-4-hydroxy-benzonitrile; (BROMOXYNIL); ethyl 2-{[(4-chloro-6-methoxy-2-pyrimidinyl)-aminocarbonyl-]aminosulphonyl}-benzoate (CHLORIMURON); 2-chloro-N-{[(4-methoxy-6-methyl-1,3,5-triazin-2-yl)-amino]-carbonyl}-benzenesulphonamide (CHLORSULFURON); N,N-dimethyl-N'-( 3-chloro-4-methylphenyl)-urea (CHLORTOLURON); 2-[4-(2,4-dichlorophenoxy)-phenoxy]propionic acid, its methyl ester or its ethyl ester (DICLOFOP); 2-[(2-chlorophenyl)-methyl]-4,4-dimethylisoxazolidin-3-one (DIMETHAZONE); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); methyl-2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl-]3-quinolinecarboxylic acid (IMAZAQUIN); 3,5-diiodo-4-hydroxybenzonitrile (IOXYNIL); N,N-dimethyl-N'-(4-iso-propylphenyl)-urea (ISOPROTURON); (2-methyl-4-chlorophenoxy)-acetic acid (MCPA); (4-chloro-2-methylphenoxy)propionic acid (MCPP); N-methyl-2-(1,3-benzothiazol-2-yloxy)-acetanilide (MEFENACET);2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); N-(1-ethylpropyl)-3,4-dimethyl-2,6-dinitroaniline (PENDIMETHALIN); O-(6-chloro-3-phenylpyridazin-4-yl)-S-octyl thiocarbonate (PYRIDATE); 4-ethylamino-2-t-butylamino-6-methylthio-s-triazine (TERBUTRYNE); methyl 3-[[[[(4-methoxy-6-methyl-1,3,5-triazin-2-yl)-amino]carbonyl]-amino]-sulphonyl]-thiophene-2-carboxylate (THIAMETURON); S-(2,3,3-trichloroallyl) N,N-diisopropylthiocarbamate (TRIALLATE);2,6-dinitro-4-trifluoromethyl-N,N-dipropylaniline (TRIFLURALIN). Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

The preparation and use of the active compounds according to the invention can be seen from the following examples.

PREPARATION EXAMPLES Example 1

Example 1

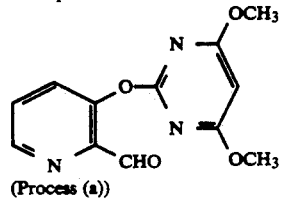

(Process (a))

A solution of 8.0 g (0.03 mol) of 2-hydroxymethyl-3-(4,6-dimethoxy-pyrimidin-2-yl-oxy)-pyridine in chloroform (250 ml) is heated to the boil. 4 Portions of 15 g of manganese(IV) oxide each (which totals 0.69 mol) are added in the course of 4 hours; the mixture is stirred under reflux for a total of 5 hours. The mixture is subsequently filtered, and the solvent is carefully removed from the filtrate by distillation under a water pump vacuum.

7.3 g (92% of theory) of 2-formyl-3-(4,6-dimethoxypyrimidin-2-yl-oxy)-pyridine are obtained as a solid residue of melting point 76° C.

Example 2

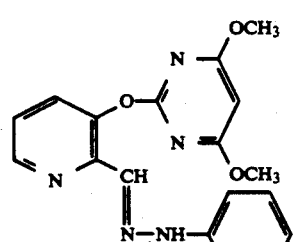

(Process (b))

A mixture of 1.56 g (6 mmol) of 3-(4,6-dimethoxypyrimidin-2-yl-oxy)-pyridin-2-aldehyde, 0.66 g (6 mmol) of phenylhydrazine and 40 ml of toluene is stirred for ½ hour at 20° C. and subsequently concentrated. The residue is brought to crystallisation using petroleum ether, and the crystalline product is isolated by filtration with suction.

2.0 g (95% of theory) of 3-(4,6-dimethoxy-pyrimidin-2-yl-oxy)-pyridin-2-aldehyde phenylhydrazone of melting point 118° C. (decomp.) are obtained.

Example 3

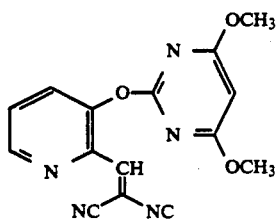

(Process (b))

A mixture of 1.56 g (6 mmol) of 3-(4,6-dimethoxypyrimidin-2-yl-oxy)-pyridin-2-aldehyde, 0.40 g (6 mmol) of malononitrile, 0.2 g of ammonium acetate and 80 ml of toluene is stirred for 2 hours at 20° C. The mixture is subsequently concentrated and the residue is brought to crystallisation using petroleum ether. The crystalline product is isolated by filtration with suction.

1.2 g (65% of theory) of α-(3-(4,6-dimethoxypyrimidin-2-yl-oxy)-pyridin-2-yl)-methylene-malononitrile of melting point 120° C. (decomp.) are obtained.

The compounds of the formula (I) — or of the formulae (IA) or (IB) — which are listed by way of example in Table 1 below can also be prepared analogously to Examples 1 to 3 and in accordance with the general description of the preparation processes according to the invention.

TABLE 1

Examples of the compounds of the formula (IA)

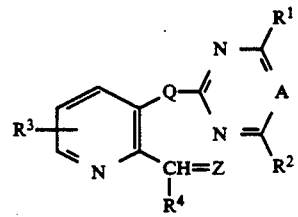

(IA)

| Example No. | A | Q | $R^1$ | $R^2$ | $R^3$ | $R^4$ | Z | Melting point (°C.) |
|---|---|---|---|---|---|---|---|---|
| 4 | CH | O | OCH$_3$ | OCH$_3$ | H | H | N—NH—C$_6$H$_4$—Cl | 137 |
| 5 | CH | O | OCH$_3$ | OCH$_3$ | H | H | N—NH—C$_6$H$_3$(F)(F) | 172 |
| 6 | CH | O | OCH$_3$ | OCH$_3$ | H | H | N—N(CH$_3$)—C$_6$H$_5$ | amorphous |
| 7 | CH | O | OCH$_3$ | OCH$_3$ | H | H | N—NH—SO$_2$—CH$_3$ | 112 |
| 8 | CH | O | OCH$_3$ | OCH$_3$ | H | H | N—NH—C$_6$H$_4$—Br | 109 |
| 9 | CH | O | OCH$_3$ | OCH$_3$ | H | H | N—NH—C$_6$H$_4$—CH$_3$ | 116 |
| 10 | CH | O | OCH$_3$ | OCH$_3$ | H | H | N—OH | 121 |
| 11 | CH | O | OCH$_3$ | OCH$_3$ | H | H | N—NH—C$_6$H$_4$—F | 166 |

TABLE 1-continued

Examples of the compounds of the formula (IA)

(IA)

| Example No. | A | Q | R¹ | R² | R³ | R⁴ | Z | Melting point (°C.) |
|---|---|---|---|---|---|---|---|---|
| 12 | CH | O | OCH₃ | OCH₃ | H | H | N—NH—C₆H₄—CF₃ (4-CF₃) | 55 |
| 13 | CH | O | OCH₃ | OCH₃ | H | H | N—NH—C₆H₃—F,F (2,4-F₂) | 142 |
| 14 | CH | O | OCH₃ | OCH₃ | H | H | N—NH—C₆H₄—Cl (2-Cl) | 138 |
| 15 | CH | O | OCH₃ | OCH₃ | H | H | N—NH—C₆H₃(Cl)—SO₂CF₃ | 168 |
| 16 | CH | O | OCH₃ | OCH₃ | H | H | N—NH—C₆H₄—Cl (3-Cl) | 147 |
| 17 | CH | O | OCH₃ | OCH₃ | H | H | N—NH—C₆H₃—Cl,Cl (2,4-Cl₂) | 132 |
| 18 | CH | O | OCH₃ | OCH₃ | H | H | N—NH—C₆H₃—Cl,Cl (2,5-Cl₂) | 163 |
| 19 | CH | O | OCH₃ | OCH₃ | H | H | N—NH—C₆H₃—Cl,Cl (2,6-Cl₂) | 111 |

TABLE 1-continued
Examples of the compounds of the formula (IA)

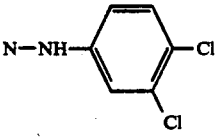

(IA)

| Example No. | A | Q | R¹ | R² | R³ | R⁴ | Z | Melting point (°C.) |
|---|---|---|---|---|---|---|---|---|
| 20 | CH | O | OCH₃ | OCH₃ | H | H | N—NH—C₆H₃(Cl)(Cl) (3,4-dichlorophenyl) | 75 |
| 21 | CH | O | OCH₃ | OCH₃ | H | H | N—NH—C₆H₄(NO₂) (2-NO₂) | 102 |
| 22 | CH | O | OCH₃ | OCH₃ | H | H | N—NH—C₆H₄(NO₂) (3-NO₂) | 153 |
| 23 | CH | O | OCH₃ | OCH₃ | H | H | N—NH—C₆H₄—NO₂ (4-NO₂) | 187 |
| 24 | CH | O | OCH₃ | OCH₃ | H | H | N—NH—C₆H₄(CH₃) (2-CH₃) | 117 |
| 25 | CH | O | OCH₃ | OCH₃ | H | H | N—NH—C₆H₄—CN (4-CN) | 185 |
| 26 | CH | O | OCH₃ | OCH₃ | H | H | N—NH—C₆H₄(CF₃) (3-CF₃) | 126 |
| 27 | CH | O | OCH₃ | OCH₃ | H | H | N—N(CH₃)₂ | (amorphous) |
| 28 | CH | O | OCH₃ | OCH₃ | H | H | N—NH—CO—CH₃ | 145 |
| 29 | CH | O | OCH₃ | OCH₃ | H | H | N—NH—CO—C₆H₅ | 128 |
| 30 | CH | O | OCH₃ | OCH₃ | H | H | N—N(CH(CH₃)₂)—C₆H₅ | 88 |

TABLE 1-continued

Examples of the compounds of the formula (IA)

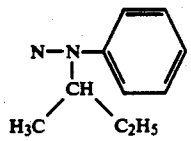

(IA)

| Example No. | A | Q | R¹ | R² | R³ | R⁴ | Z | Melting point (°C.) |
|---|---|---|---|---|---|---|---|---|
| 31 | CH | O | OCH₃ | OCH₃ | H | H | 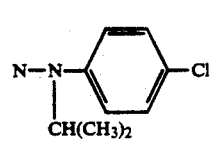 | 90 |
| 32 | CH | O | OCH₃ | OCH₃ | H | H | 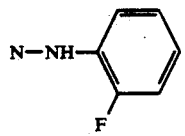 | 62 |
| 33 | CH | O | OCH₃ | OCH₃ | H | H | 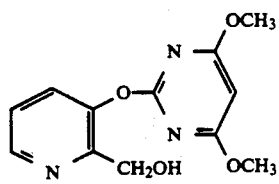 | 132 |

Starting Substances of the Formula (II)

Example (II-1)

A mixture of 18.3 g (0.06 mol) of ethyl 3-(4,6-dimethoxypyrimidine-2-yl-oxy)-pyridin-2-carboxylate and 200 ml of ethanol is cooled to 0° C. to 5° C., and 6.5 g (0.17 mol) of sodium borohydride are added in portions, with stirring. A solution of 10 g of calcium chloride in 60 ml of ethanol is then added dropwise, and the mixture is stirred for 1 hour at 0° C. to 5° C. To remove the excess of borohydride, the mixture is subsequently acidified using hydrochloric acid and then again rendered weakly alkaline by adding sodium carbonate. The mixture is extracted using diethyl ether, the extraction solution is concentrated, the residue is brought to crystallisation by trituration with diethyl ether/petroleum ether, and the product is isolated by filtration with suction.

9.3 g (59% of theory) of 2-hydroxymethyl-3-(4,6-dimethoxy-pyrimidin-2-yl-oxy)-pyridine of melting point 115° C. are obtained.

Use Examples

Example A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient in this case to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example the compounds of Preparation Examples (2) and (3) show a powerful action against weeds while having good compatibility with crop plants such as, for example, soya.

Example B

Post-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 1000 l of water/ha. After three weeks, the degree of damage to the plants is rated in % damage in comparison to the development of the untreated control. The figures denote:

0% =no action (like untreated control)
100% =total destruction

In this test, for example the compounds of Preparation Examples (1), (2) and (3) show a powerful action against weeds while having good compatibility with crop plants such as, for example, maize.

We claim:

1. Substituted pyridines of the formula (I)

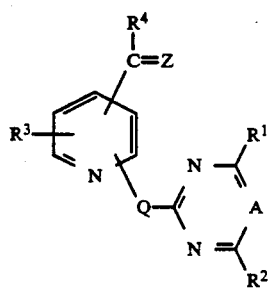

in which
A represents a C-X group, where X represents hydrogen or halogen,
Q represents oxygen or sulphur,
$R^1$ and $R^2$ are identical or different and represent hydrogen, halogen, $C_1$–$C_4$-alkyl, $C_1$–$C_4$-halogenoalkyl, $C_1$–$C_2$-alkoxy-$C_1$–$C_2$-alkyl, $C_1$–$C_4$-alkoxy, $C_1$–$C_4$-halogenoalkoxy, $C_1$–$C_4$-alkylthio, $C_1$–$C_4$-alkylamino or di-($C_1$–$C_2$-alkyl)-amino,
$R^3$ represents hydrogen, amino, nitro, hydroxyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylamino, di-($C_1$–$C_2$-alkyl)-amino, $C_1$–$C_4$-alkyl-carbonylamino, $C_1$–$C_4$-alkoxy-carbonylamino or $C_1$–$C_4$-alkylsulphonylamino,
$R^4$ represents hydrogen or $C_1$–$C_4$-alkyl and
Z represents one of the groups below: N-$R^5$ or

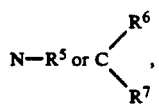

where
$R^5$ represents hydrogen, hydroxyl or amino, or represents in each case optionally halogen-substituted $C_1$–$C_6$-alkyl, $C_3$–$C_6$-alkenyl, $C_3$–$C_6$-alkinyl, $C_1$–$C_6$-alkoxy, $C_3$–$C_6$-alkenyloxy, $C_1$–$C_4$-alkoxy-carbonyl-$C_1$–$C_2$-alkoxy, $C_1$–$C_6$-alkylamino, di-($C_1$–$C_2$-alkyl)-amino, $C_1$–$C_6$-alkylcarbonylamino, $C_1$–$C_6$-alkoxy-carbonylamino, $C_1$–$C_6$-alkyl-sulphonylamino, or represents phenyl, phenyl-$C_1$–$C_4$-alkyl, phenoxy, phenyl-$C_1$–$C_4$-alkoxy, phenylamino, phenyl-$C_1$–$C_4$-alkylamino, N-($C_1$–$C_4$-alkyl)-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxy-carbonyl and/or di-($C_1$–$C_2$-alkyl)amino,
$R^6$ represents hydrogen, halogen, cyano, carboxyl, $C_1$–$C_6$-alkoxy-carbonyl, $C_1$–$C_6$-alkylcarbonylamino or di-($C_1$–$C_4$-alkoxy)-phosphoryl and
$R^7$ represents formyl, cyano, carboxyl, hydroxymethyl or carbamoyl, or represents $C_1$–$C_6$-alkoxycarbonyl, $C_5$–$C_6$-cycloalkyloxy-carbonyl, $C_1$–$C_6$-alkylthiocarbonyl, $C_1$–$C_6$-alkylamino-carbonyl or $C_5$–$C_6$-cycloalkylamino-carbonyl, each of which is optionally substituted by halogen, carboxyl or $C_1$–$C_4$-alkoxycarbonyl, or represents di-($C_1$–$C_2$-alkyl)-aminocarbonyl, or represents $C_1$–$C_4$-alkylamino-carbonyl-$C_1$–$C_4$-alkoxy-carbonyl, or represents di-($C_1$–$C_2$-alkyl)-amino-carbonyl-$C_1$–$C_4$-alkoxy-carbonyl, or represents phenylaminocarbonyl-$C_1$–$C_4$-alkoxycarbonyl, or represents N-methyl-N-phenylamino-carbonyl-$C_1$–$C_4$-alkoxy-carbonyl, or represents pyrrolidinylcarbonyl, piperidinyl-carbonyl, morpholinylcarbonyl or piperazinylcarbonyl, each of which is optionally substituted by methyl and/or ethyl, or represents phenoxycarbonyl, phenyl-$C_1$–$C_4$-alkoxycarbonyl, furylmethoxycarbonyl, thienylmethoxycarbonyl, phenylthiocarbonyl, phenyl-$C_1$–$C_4$-alkylthio-carbonyl, phenylaminocarbonyl, phenyl-$C_1$–$C_4$-alkylamino-carbonyl, N-($C_1$–$C_4$-alkyl)-N-phenylamino-carbonyl or phenylhydrazino-carbonyl or $C_1$–$C_4$-alkylhydrazinocarbonyl, each of which is optionally substituted by nitro, amino, cyano, carboxyl, halogen, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkoxy-carbonyl and/or di-($C_1$–$C_2$-alkyl)-amino, or represents phthalimidoxycarbonyl, or together with $R^6$ represents the group —CO—O—(CH$_2$)$_n$—, where n represents the numbers 1 to 4.

2. Substituted pyridines of the formula (I) according to claim 1, in which
A represents a CH group,
Q represents oxygen,
$R^1$ represents hydrogen, chlorine, methyl, ethyl, trifluoromethyl, methoxymethyl, methoxy, ethoxy, difluoromethoxy, methylthio, methylamino, ethylamino or dimethylamino,
$R^2$ represents hydrogen, chlorine, methyl, ethyl, trifluoromethyl, methoxy, ethoxy, difluoromethoxy, methylthio, methylamino, ethylamino or dimethylamino,
$R^3$ represents hydrogen, amino, hydroxyl, fluorine, chlorine, bromine, methyl, ethyl, trifluoromethyl, methoxy, difluoromethoxy, trifluoromethoxy, methylamino, dimethylamino, acetylamino, methoxycarbonylamino or methylsulphonylamino,
$R^4$ represents hydrogen or methyl and
Z represents one of the groups below:

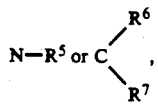

where
R$^5$ represents hydrogen, hydroxyl or amino, or represents methyl, ethyl, n-propyl, isopropyl, n-butyl, isobutyl, sec-butyl, tert-butyl, allyl, propargyl, methoxy, ethoxy, n-propoxy, isopropoxy, n-butoxy, isobutoxy, sec-butoxy, allyloxy, methoxycarbonylmethoxy, ethoxycarbonylmethoxy, methoxycarbonylethoxy, ethoxycarbonylethoxy, methylamino, ethylamino, n-propylamino, isopropylamino, n-butylamino, isobutylamino, sec-butylamino, tert-butylamino, dimethylamino, acetylamino, propionylamino, methoxycarbonylamino, ethoxycarbonylamino, methylsulphonylamino or ethylsulphonylamino, or represents phenyl, benzyl, phenoxy, benzyloxy, phenylamino, benzylamino, N-methyl-N-phenylamino, pyridylamino, pyrimidylamino, pyridylcarbonylamino, phenylcarbonylamino, furylcarbonylamino, thienylcarbonylamino or phenylsulphonylamino, each of which is optionally substituted by nitro, cyano, fluorine, chlorine, bromine, methyl, trifluoromethyl, methoxy, trifluoromethoxy, methylthio or trifluoromethylthio, R$^6$ represents hydrogen, fluorine, chlorine, cyano, carboxyl, C$_1$-C$_4$-alkoxy-carbonyl, C$_1$-C$_4$-alkylcarbonylamino, dimethoxyphosphoryl or diethoxyphosphoryl, and R$^7$ represents formyl, cyano, carboxyl, hydroxymethyl or carbamoyl, or represents C$_1$-C$_4$-alkoxycarbonyl, C$_5$C$_6$-cycloalkyloxy-carbonyl, C$_1$-C$_4$-alkylthiocarbonyl, C$_1$-C$_4$-alkylamino-carbonyl or C$_5$-C$_6$-cycloalkylamino-carbonyl, each of which is optionally substituted by fluorine, chlorine, carboxyl or C$_1$-C$_4$-alkoxy-carbonyl, or represents dimethylaminocarbonyl, or represents C$_1$-C$_4$-alkylaminocarbonyl-C$_1$-C$_4$-alkoxy-carbonyl, or represents dimethylaminocarbonyl-C$_1$-C$_4$-alkoxy-carbonyl, or represents N-methyl-N-phenylaminocarbonyl-C$_1$-C$_4$-alkoxy-carbonyl, or represents pyrrolidinylcarbonyl, piperidinylcarbonyl, morpholinylcarbonyl or piperazinyl-carbonyl, each of which is optionally substituted by methyl and/or ethyl, or represents phenoxycarbonyl, benzyloxycarbonyl, phenylthiocarbonyl, benzylthiocarbonyl, phenylaminocarbonyl, benzylaminocarbonyl, N-methyl-N-phenylaminocarbonyl, phenylhydrazinocarbonyl, each of which is optionally substituted by nitro, cyano, fluorine, chlorine, bromine, methyl, trifluoromethyl, methoxy, trifluoromethoxy, methylthio or trifluoromethylthio, or represents phthalimidoxycarbonyl, or together with R$^6$ represents the group —CO—O—CH$_2$CH$_2$—.

3. Substituted pyridines of the formulae (IA) and (IB)

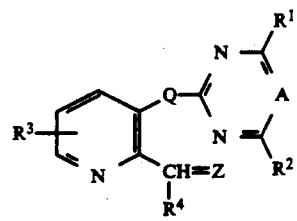

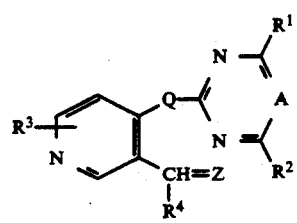

in which A, Q, R$^1$, R$^2$, R$^3$, R$^4$ and Z have the meaning given in claim 2.

4. Substituted pyridines of the formula (IA) or (IB) according to claim 3, where
A represents a CH group,
Q represents oxygen,
R$^1$ represents methoxy,
R$^2$ represents methoxy,
R$^3$ represents hydrogen or fluorine,
R$^4$ represents hydrogen 5. Substituted pyridine of the following formula:

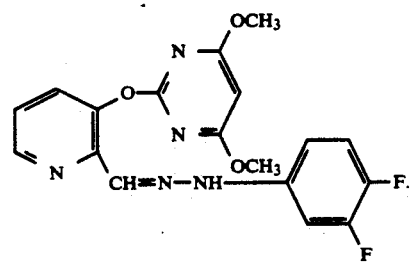

6. Herbicidal compositions comprising an effective amount of at least one substituted pyridine derivative of the formula (I) according to claim 1.

7. A method of combating undesired plants comprising treating the plants with an effective amount of a composition according to claim 6.

* * * * *

UNITED STATES PATENT AND TRADEMARK OFFICE
CERTIFICATE OF CORRECTION

PATENT NO. : 5,215,569

DATED : June 1, 1993

INVENTOR(S) : Drewes et al.

It is certified that error appears in the above-identified patent and that said Letters Patent is hereby corrected as shown below:

Col. 25, line 36    After " $C_5$ " insert -- - --.

Signed and Sealed this

Thirtieth Day of August, 1994

Attest:

BRUCE LEHMAN

*Attesting Officer*    *Commissioner of Patents and Trademarks*